(12) United States Patent
Koehler et al.

(10) Patent No.: US 9,194,844 B2
(45) Date of Patent: Nov. 24, 2015

(54) DESTRUCTION-FREE AND CONTACTLESS INSPECTION METHOD AND INSPECTION APPARATUS FOR SURFACES OF COMPONENTS WITH ULTRASOUND WAVES

(75) Inventors: Bernd Koehler, Dresden (DE); Martin Barth, Dresden (DE); Joachim Bamberg, Dachau (DE); Hans-Uwe Baron, Munich (DE)

(73) Assignees: FRAUNHOFER-GESELLSCHAFT ZUR FOERDERUNG DER ANGEWANDTEN FORSCHUNG E.V., Munich (DE); MTU AERO ENGINES GMBH, Munich (DE)

( * ) Notice: Subject to any disclaimer, the term of this patent is extended or adjusted under 35 U.S.C. 154(b) by 368 days.

(21) Appl. No.: 13/810,528

(22) PCT Filed: Jul. 14, 2011

(86) PCT No.: PCT/DE2011/001424
§ 371 (c)(1),
(2), (4) Date: Jan. 16, 2013

(87) PCT Pub. No.: WO2012/028125
PCT Pub. Date: Mar. 8, 2012

(65) Prior Publication Data
US 2013/0111995 A1    May 9, 2013

(30) Foreign Application Priority Data

Jul. 16, 2010   (DE) .......................... 10 2010 032 117

(51) Int. Cl.
*G01N 29/22*     (2006.01)
*G01N 29/07*     (2006.01)
(Continued)

(52) U.S. Cl.
CPC ............ *G01N 29/221* (2013.01); *G01N 29/075* (2013.01);
(Continued)

(58) Field of Classification Search
CPC ..... G01N 29/04; G01N 29/075; G01N 29/11; G01N 29/221; G01N 29/262; G01N 29/2487
USPC .................................... 73/596–600, 627–634
See application file for complete search history.

(56) References Cited

U.S. PATENT DOCUMENTS

| | | | | |
|---|---|---|---|---|
| 4,098,129 | A | * | 7/1978 | Deblaere et al. ................. 73/599 |
| 4,541,281 | A | * | 9/1985 | Chubachi et al. ............... 73/606 |
| 4,592,034 | A | * | 5/1986 | Sachse et al. .................. 367/127 |
| 7,331,234 | B2 | * | 2/2008 | Tsujita et al. ................... 73/606 |

(Continued)

FOREIGN PATENT DOCUMENTS

EP          0487871 A1      3/1992

*Primary Examiner* — Helen Kwok
(74) *Attorney, Agent, or Firm* — Jacobson Holman, PLLC

(57) ABSTRACT

The invention relates to a method of nondestructive and contactless testing of components (3), wherein ultrasonic waves (6) are irradiated onto the surface of the component (3) at a predefinable, non-perpendicular angle of incidence (9) using an ultrasonic transmission sound transducer (1) arranged spaced apart from the surface of the component (3) and the intensity of the ultrasonic waves (7) reflected from the surface of the component (3) is detected with time resolution and/or frequency resolution by the antenna array elements (2*n*) of an ultrasonic antenna array (2) configured for detecting ultrasonic waves (7) and the phase shift of the ultrasonic waves guided at the surface of the test body is determined therefrom with respect to the ultrasonic waves (7) directly reflected at the surface of the component (3).

16 Claims, 6 Drawing Sheets

Figure 1:
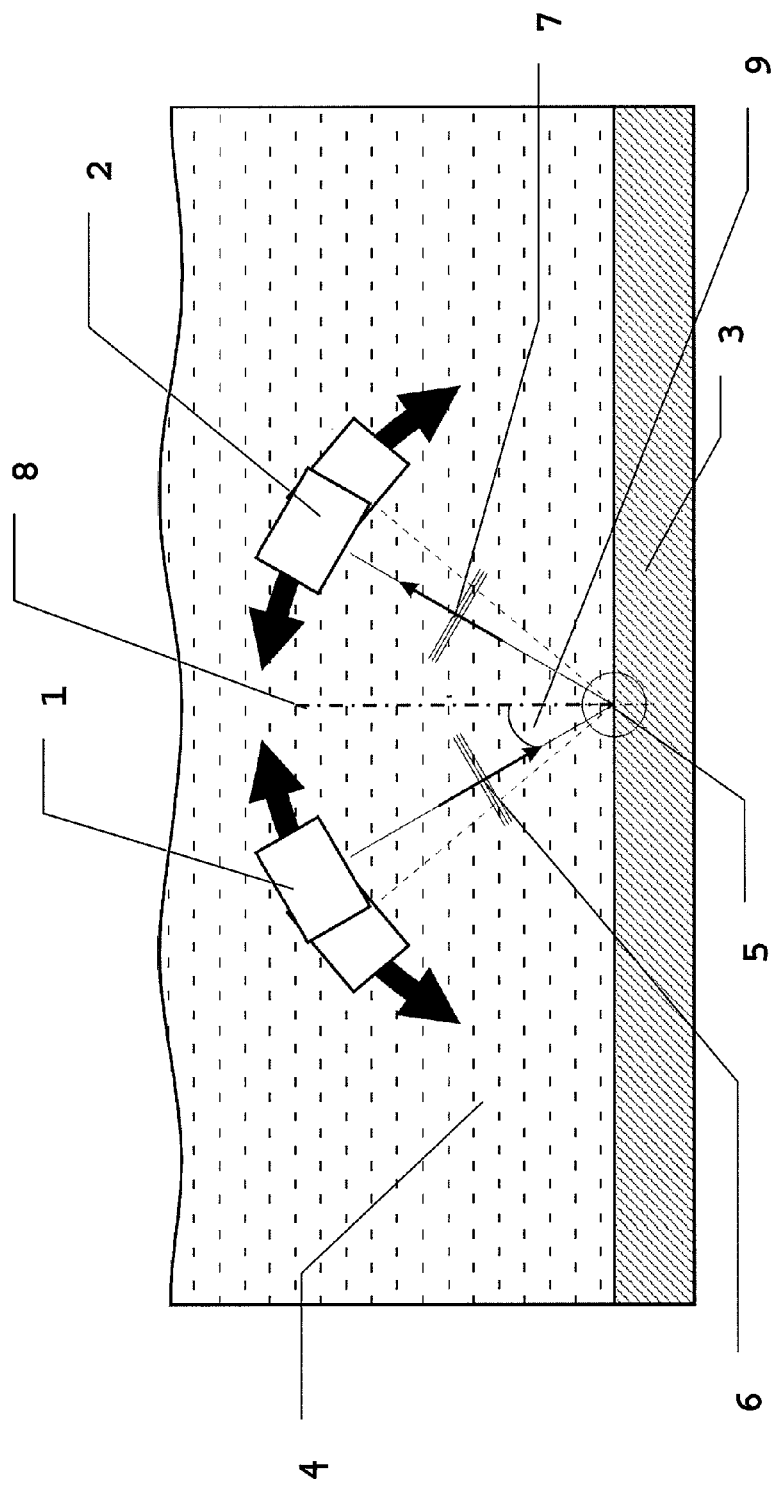

(51) Int. Cl.
*G01N 29/11* (2006.01)
*G01N 29/24* (2006.01)
*G01N 29/26* (2006.01)

(52) U.S. Cl.
CPC ............ *G01N 29/11* (2013.01); *G01N 29/2487* (2013.01); *G01N 29/262* (2013.01); *G01N 2291/044* (2013.01); *G01N 2291/056* (2013.01); *G01N 2291/106* (2013.01)

(56) References Cited

U.S. PATENT DOCUMENTS

| | | | | |
|---|---|---|---|---|
| 7,421,900 | B2* | 9/2008 | Karasawa et al. | 73/621 |
| 8,038,616 | B2* | 10/2011 | Angelsen et al. | 600/437 |
| 8,234,923 | B2* | 8/2012 | Ramamurthy et al. | 73/606 |
| 8,490,489 | B2* | 7/2013 | Randall et al. | 73/602 |
| 2009/0019937 | A1* | 1/2009 | Deemer et al. | 73/660 |

* cited by examiner

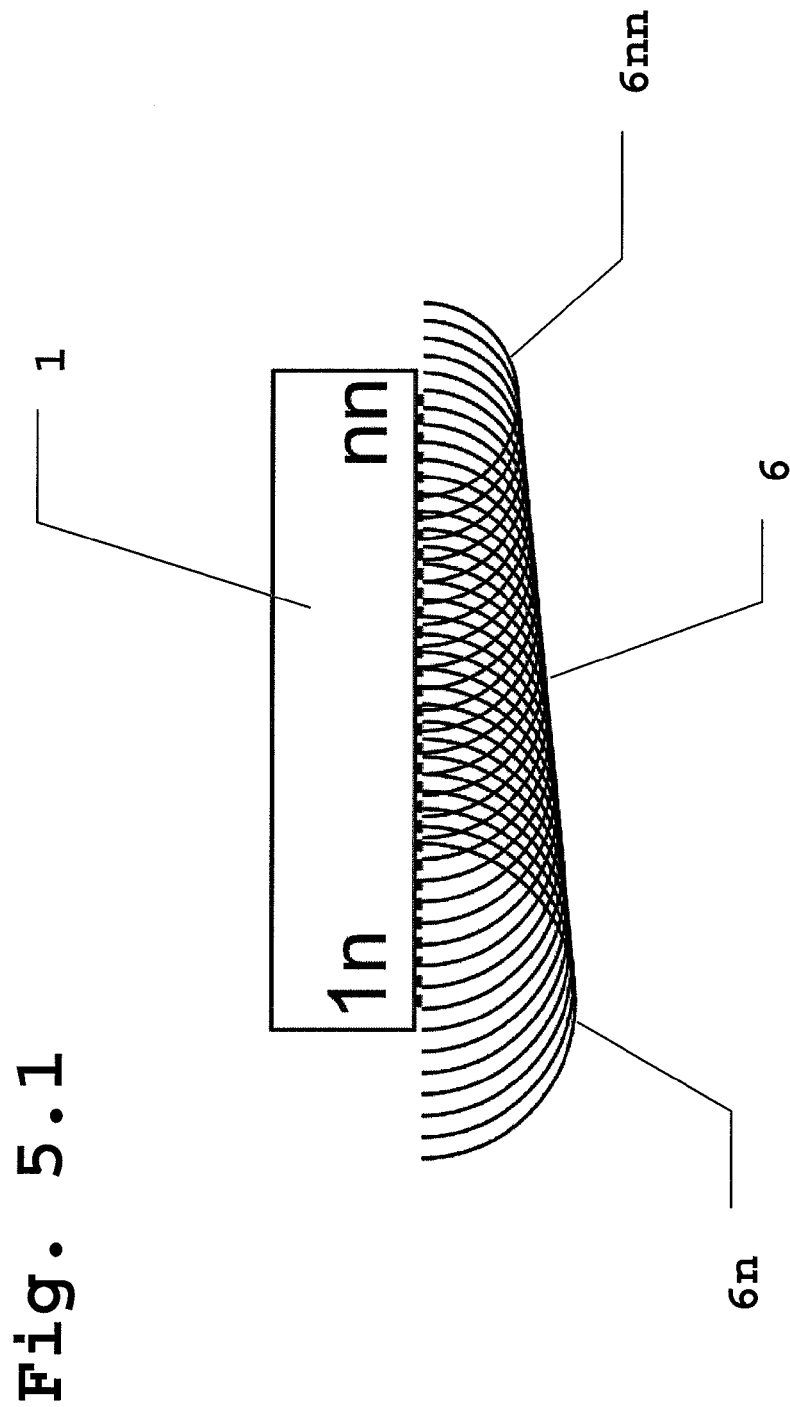
Fig. 5.1

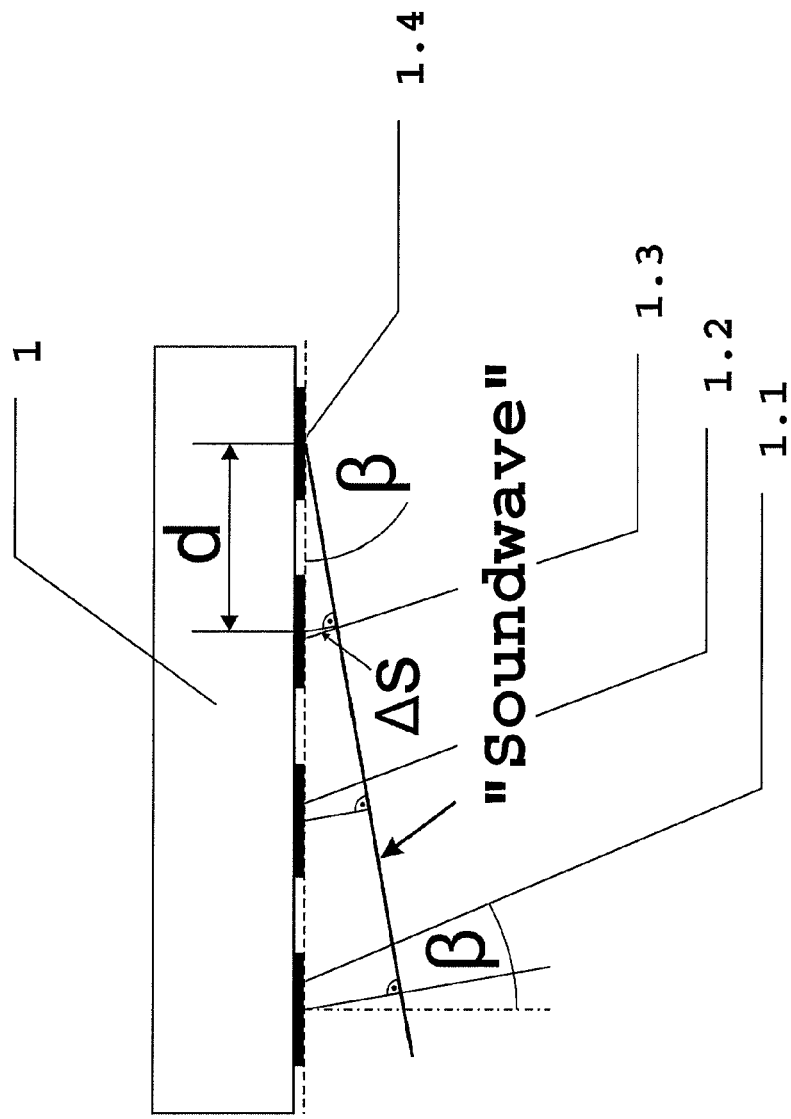
Fig. 5.2

DESTRUCTION-FREE AND CONTACTLESS INSPECTION METHOD AND INSPECTION APPARATUS FOR SURFACES OF COMPONENTS WITH ULTRASOUND WAVES

This is a national stage of PCT/DE11/001424 filed Jul. 14, 2011 and published in German, which has a priority of German no. 10 2010 032 117.6 filed Jul. 16, 2010, hereby incorporated by reference.

The invention relates to a nondestructive and contactless test method and to a test apparatus for surfaces of components, each working with ultrasonic waves which are irradiated onto the component surface at a non-perpendicular angle of irradiation.

The principle of an acoustic goniometer is known for inspecting acoustic properties of components. In this respect, it is a question of an ultrasonic goniometer which is applied to a component at a specific spacing in a liquid couplant. Two ultrasound transducers are directed toward the same point of the surface of the component such that the ultrasonic waves emitted by a sound transducer configured for emitting ultrasonic waves impact exactly on a sound transducer configured for detecting ultrasonic waves after their refection at the surface of the component. Both sound transducers are accordingly always directed at the same angle relative to the normal of the surface of the component and are arranged opposite one another. Both sound transducers can be pivoted mechanically about the point of incidence of the ultrasonic waves on the surface of the component to vary the angle of irradiation of the ultrasonic waves.

A goniometer designed in this manner allows the detection of the angle-dependent profile of the ultrasonic wave reflection coefficient of the surface of the component. The acoustic velocities of different ultrasonic waves in the component can be determined from this. In this respect, one talks of the critical angle of ultrasonic wave reflection when the angle of refraction of the longitudinal waves or transverse waves refracted into the component approaches 90° or guided waves such as surface waves or plate waves (Lamb waves) are excited to a maximum. At critical angles, the intensity of the reflected ultrasonic waves becomes a maximum or—on excitation of guided waves—a minimum.

The reflection profile of the ultrasonic waves can also be determined in dependence on frequency by a suitable choice of the sound transducers used and by a suitable echo data analysis. Propagation speeds of the ultrasonic waves, that is their dispersion, can thereby also be determined which are dependent on the frequency of the ultrasonic waves. Properties of the component to be tested can be characterized in dependence on depth from the frequency dependence or wavelength dependence of the ultrasonic waves guided at the surface of the component.

In machining processes of surface strengthening, the structure of a component is modified and internal compressive stresses are introduced. The shot peening of surfaces represents one such possible processing. The internal compressive stresses thereby introduced are of great importance for the component behavior in operation and the presence of internal compressive stresses must also still have to be detected after a certain component service life. The internal stresses can relax during operation, for example, and the structural changes introduced by the surface strengthening may be healed, which can endanger the proper function of the component. To detect that such a process has not yet taken place, the dependence of the acoustic velocity of the ultrasonic waves guided at the surface of the component can be measured using a goniometer.

The ultrasound electronics used in goniometers known from the prior art have a very simple design; however, the mechanical construction for predefining the angle of irradiation of the ultrasonic waves is very complex. A disadvantage results through the common axis of rotation of the sound transducers at the point of incidence of the ultrasonic waves on the surface of the component. Centers of rotation arranged to the side of the component or rails with a circular curvature have to be used at which the sound transducers have to be displaceably installed. Rails which run in fixed bearings can also be used; however, the sound transducers in every case have to be able to be moved with mirror symmetry and as free of play as possible. In addition, such a mechanical construction is inflexible and is in particular not precise enough for measurements with high demands on measuring precision or is limited by the production precision of the above-mentioned components.

It is therefore the object of the invention to provide a method and an apparatus for carrying out said method which where possible does not require any mechanical construction for predefining the angle of irradiation of the ultrasonic waves. It is a further object of the present invention to improve the precision of the component testing of conventional goniometers. It is furthermore an object of the invention to allow a greater flexibility and better recognition of component flaws as well as the determination of material properties (elastic moduli) and their depth-dependent variation in the area close to the surface. It is in particular an object of the invention to detect a change in the component properties by a surface strengthening processing such as by shot peening.

In accordance with the invention, this object is achieved by a method having the features of claim 1. In this respect, an apparatus in accordance with claim 12 can be used. Advantageous aspects and further developments can be achieved using the features designated in the subordinate claims.

The achieve the above-named objects, the detection of ultrasonic waves should take place by an ultrasonic antenna array (also called a phased array) using its antenna array elements in a frequency-resolved and/or time-resolved manner and the phase shift of these guided ultrasonic waves with respect to the directly reflected ultrasonic waves should the determined from this.

In addition, the frequency dependence of the propagation speed of the ultrasonic waves guided at the surface of the component can also be determined from this.

The solution in accordance with the invention will be described in detail in the following with reference to a plurality of embodiments. The individual features in accordance with the invention presented here cannot only occur in a combination such as is shown in the individual, specific advantageous embodiments, but can also be formed or used in any other combination possibilities within the framework of the present invention.

A method in accordance with the invention allows the nondestructive and contactless testing of components by the irradiation of ultrasonic waves onto the surface of the component at a predefinable angle of irradiation which can adopt a value between 0 and 90 degrees, that is of the surface normal and a tangent at the surface of the component. The irradiation therefore does not place perpendicular to the surface of the component. After the irradiation of the ultrasonic waves at a point of incidence at the surface of the component, the intensity of the ultrasonic waves reflected at the surface of the component is detected using an ultrasonic antenna array configured for detecting ultrasonic waves. In this respect, the intensity of the reflected ultrasonic waves is detected with frequency resolution or time resolution by the antenna array elements of the antenna array formed for detecting ultrasonic waves; it is particularly advantageous to detect the ultrasonic intensity with both time resolution and frequency resolution.

In a method in accordance with the invention, the angle of irradiation of the ultrasonic waves can be varied by the spatial arrangement of the antenna array elements of the antenna array configured for detecting ultrasonic waves, without a mechanical variation of the position or orientation of the antenna array configured for detecting ultrasonic waves being necessary. Instead, it is possible to work with a varied angle of irradiation and the varied angle of reflection resulting therefrom of the ultrasonic waves reflected at the surface of the component by a suitable weighting and detection of the ultrasonic wave intensity, in time, space and/or amplitude, at the antenna array elements of the antenna array configured for detecting ultrasonic waves.

The frequency dependence of the propagation speed of the ultrasonic waves guided at the surface of the component can be determined from the detected intensities of the reflected ultrasonic waves. These ultrasonic waves guided at the surface of the component can, for example, by Rayleigh waves and/or Lamb waves. A characteristic angle of incidence, at which the measured intensity of the reflected ultrasonic wave has a minimum, results for each ultrasonic wave frequency. Conversely, it follows from that that the ultrasonic waves guided at the surface of the component are excited in the best possible manner at this angle of irradiation. Using the relationship $$c_{US}(f) = \frac{c_{medium}}{\sin(\alpha_{min}(f))} \quad (1)$$

the propagation speed of the ultrasonic waves $c_{US}(f)$ guided at the surface of the component can be determined from the frequency dependence of the angle of incidence $\alpha$ with the minimal reflected intensity, $\alpha_{min}(f)$, with frequency dependence using the ultrasonic wave propagation speed $c_{medium}$ assumed as known of the medium surrounding the component, for example water, gel or air.

Figure 2:
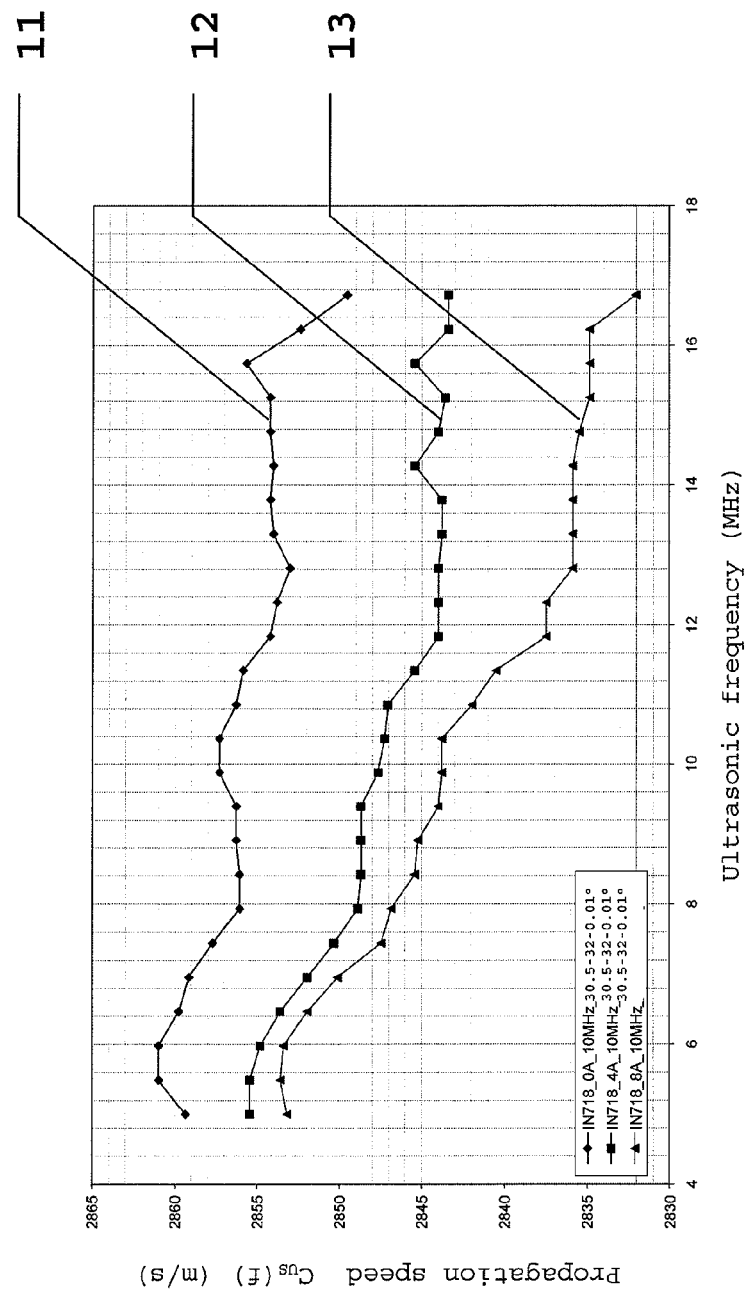

The frequency-dependent propagation speed of the ultrasonic waves $c_{US}(f)$ guided at the surface of the component depends on the properties of the component surface. FIG. 2 shows an example measurement of $c_{US}(f)$ over an ultrasound frequency range of 5 to 17 MHz. The measured value distribution 11 marked by diamonds (♦) for $c_{US}(f)$ in this respect originates from a component which was not exposed to any shot peening processing at the surface. The measured value distribution 12 marked by squares (■) of the $c_{US}(f)$ was detected at a component which was exposed to a shot peening intensity of 4 Almen. The measured value distribution 13 marked by triangles (▲) of the $c_{US}(f)$ was detected at a component which was exposed to a shot peening intensity of 8 Almen.

The measured value distributions in accordance with FIG. 2 in this respect represent a first step of the measured data evaluation and can also be detected with spatial resolution over the surface of the component after carrying out a method in accordance with the invention.

In a further embodiment of the method in accordance with the invention, the antenna array elements of the antenna array configured for detecting ultrasonic waves can be used for detecting the spatial intensity profile of the reflected ultrasound waves with the antenna array formed or used for detecting ultrasonic waves. Due to the known spatial arrangement, the antenna array elements allow the detection of the spatial intensity profile of the reflected ultrasonic waves which is formed by interference of the ultrasonic waves reflected at the surface of the component with ultrasonic waves which are radiated back by the ultrasonic waves guided at the surface of the component.

A phase difference between the ultrasonic waves guided at the surface of the component and the ultrasonic waves reflected directly at the surface of the component can be determined by the detection of the spatial ultrasonic intensity profile caused by interference at the antenna array configured for detecting ultrasonic waves. This phase difference can be a consequence of the properties of the component to be tested and thereby allows conclusions on further properties of the component and its surface.

In an advantageous embodiment of the method in accordance with the invention, an ultrasonic antenna array is used which is configured for emitting ultrasonic waves. In a line antenna array which is advantageously used, individually controllable or regulable antenna array elements are arranged next to one another in strip form with a spacing which is as small as possible. Each antenna array element is configured for emitting ultrasonic waves. The individual emitted ultrasonic waves can be superimposed to form a resulting ultrasonic wave by a time delay of the excitation of the individual antenna array elements and can thereby be emitted at a specific angle by the antenna array. In so doing, the angle of irradiation β of the resulting ultrasonic wave with respect to the plane of the antenna array elements results according to the relationship $$\beta = \sin^{-1}\left(\frac{\Delta t \cdot c_{medium}}{d}\right), \quad (2)$$

where d is the spatial distance of the antenna array elements from one another and $\Delta t$ is the time difference of the maximum of excitation of two respective adjacent antenna array elements. In this manner, the angle of irradiation of the ultrasonic waves on the surface of the component can thus be varied without moving the ultrasonic antenna array. Using the equation (2), the delay $\Delta t$ between the received signals of respective adjacent antenna array elements at the antenna array configured for detecting ultrasonic waves can be calculated which results from a specific angle of irradiation. The detected signals of the individual antenna array elements can thus be shifted with respect to one another in time before a later summing to set an angle of detection β' with maximum reception sensitivity.

A regulation of the excitation of the individual antenna array elements with a signal detection and retroaction can also be carried out based on the ultrasonic waves reflected by the antenna array configured for detecting ultrasonic waves or its antenna array elements and on the ultrasonic intensity or intensities detected by it or by them of the ultrasonic waves reflected at the surface of the component.

In a further advantageous embodiment of a method in accordance with the invention, the spatial and temporal excitation of the antenna array elements of an antenna array configured for emitting ultrasonic waves is controlled to establish a defined, resulting spatial and/or temporal intensity profile of the ultrasonic waves by interfering superimposition of the ultrasonic wave emission of the individual antenna array elements at a defined position and/or at a defined point in time.

A focusing of the ultrasonic waves irradiated onto the surface of the component can thus be achieved at the component, for example. The spatial resolution of the test method in accordance with the invention can thus be improved at the surface of the component. A test can also be made of the surface of a dynamically moved component at a defined point in time in that ultrasonic waves are irradiated onto the surface of the component at the defined point in time by an ultrasonic wave pulse by a suitable time excitation of the antenna array elements of the antenna array configured for emitting ultrasonic waves.

In accordance with Huygens principle of interference of the partial waves of all individual antenna array elements of the antenna array configured for emitting ultrasonic waves, practically any spatial and/or temporal intensity profile of the ultrasonic waves used in a method in accordance with the invention can thus also be established by a regulation of the excitation of the antenna array elements with the aid of sensors which are configured for detecting ultrasonic waves.

The detection of the ultrasonic wave intensity advantageously takes place by the antenna array provided in accordance with the invention and configured for detecting ultrasound waves and with both time resolution and frequency resolution. In an advantageous embodiment of the method in accordance with the invention, diffraction effects of the ultrasonic waves irradiated onto the surface of the component can be minimized by a temporal and/or spatial ultrasonic wave intensity distribution established in this manner.

Edge ribs and secondary lobes can also be greatly reduced in ultrasonic emission by use of a spatial window function at the ultrasound wave emitting antenna array elements of an antenna array configured for emitting ultrasonic waves. The use of a window function in the form of a Gaussian bell curve for forming the irradiated ultrasonic waves can in particular result in an intensity profile which is very similar to that of a planar ultrasonic wave, which can in particular be of advantage in the avoidance of measurement errors.

Every antenna array element of an antenna array configured for emitting ultrasonic waves can be excited individually. The ultrasonic waves reflected at the surface of the component are detected by all the antenna array elements of the antenna array configured for detecting ultrasonic waves. It is advantageous in this respect if each antenna array element emits or can emit and/or can receive a similar ultrasonic wave frequency spectrum which is wide as possible.

The spatial, time-resolved and/or frequency-resolved ultrasonic wave intensity signals of each individual antenna array element emitting ultrasonic waves detected by all the antenna array elements of the antenna array configured for detecting ultrasonic waves can be superimposed with the remaining detected ultrasonic wave intensity signals subsequent to the detection and can in so doing also be scaled. This can take place, for example, in a suitably configured data processing apparatus.

In this manner, the surface of the component can be measured in a shorter time over an actual and physical superimposition of the ultrasonic waves emitted by the antenna array elements.

In a further advantageous embodiment, in a method in accordance with the invention, work can be carried out using switchable antenna arrays which can be switched between a configuration for emitting ultrasonic waves and a configuration for detecting ultrasonic waves. In this manner, the precision of the surface testing in accordance with the invention can be increased at the component. In this respect, first an irradiation of ultrasonic waves is carried out using the first antenna array at the surface of the component which is used in this process for emitting ultrasonic waves and the intensity of the reflected ultrasonic waves is detected by the second antenna array. The operation of both antenna arrays is thereupon switched over from emission to detection and from detection to emission and the process is carried out again. In this manner, surface effects at the component can be recognized which occur by reflection in a specific direction.

In a further embodiment, work can advantageously be carried out using a single antenna array. It is in this process switched over for emitting ultrasonic waves and for detecting them so that it can itself detect the ultrasonic waves reflected by the surface of the component.

A reflector element is particularly advantageously used in such a process, whereby the ultrasonic waves initially reflected by the surface of the component are reflected back onto the surface of the component where they are reflected a further time and can be detected by the antenna array used intermittently for detecting ultrasonic waves. In such a process, two reflections of the irradiated ultrasonic waves occur at the surface of the component, which can facilitate the determination of an angle of irradiation with a minimum of detected ultrasonic wave intensity.

It is particularly advantageous if the component to be tested is arranged in a liquid bath such as water, an immersion oil or also a gel. Due to the higher density and propagation speed of ultrasonic waves $c_{medium}$ over gases and the associated higher acoustic impedance of these media a better ultrasound coupling capability at solids results, which can facilitate the component testing and surface characterization using ultrasonic waves.

In a method in accordance with the invention in which an ultrasonic reflector element is used, it is advantageous that the ultrasonic reflectivity of the reflector element is as large as possible and that ultrasonic waves can be reflected back at a range of possible angles of irradiation which is as large as possible over the surface of the component to the antenna array configured for detecting ultrasonic waves. This can be achieved, for example, using a concave element such as a parabolic shape or a hollow sphere shape.

In an apparatus for carrying out the method in accordance with the invention, a sound transducer can be configured as the antenna array and for detecting ultrasonic waves. The angle of inclination for emitting ultrasonic waves of a conventional sound transducer configured for emitting ultrasonic waves can be adjusted by pivoting about a center of rotation. The angle of irradiation of the ultrasound waves onto the surface of the component can thereby be varied without a mechanical movement of both sound transducers being necessary. The emitted ultrasonic waves can then be reflected at different points of incidence at the component and can be detected by different antenna array elements of the antenna array configured for detecting ultrasonic waves.

It is furthermore advantageous to configure the ultrasonic antenna arrays of an apparatus for carrying out the method in accordance with the invention as a line antenna array, a matrix antenna array and/or as a ring antenna array. These types of antenna array differ in their arrangement and in the configuration of the individual antenna array elements whose electronic control can be adapted to the desired embodiment of the method in accordance with the invention and to the type of the respective antenna array.

The method in accordance with the invention is particularly advantageously suitable for testing surfaces or areas of components close to the surface and for characterizing surface coatings and surface processing states of components, in particular at surface-strengthened components whose surfaces have been shot peened, for example. As already described above, a variation of the frequency dependence of the propagation speed of the ultrasonic waves guided at the surface of the component can be determined by the method in accordance with the invention in dependence on the ball peening intensity of a ball peening processing carried out at the component. The magnitude of the surface strengthening by structural modifications which can be derived therefrom and the introduction of internal compressive stresses are of importance, for example, with components subject to high loads which are used in engines in the aeronautic industry or in ships. The marginal strengthening results in a modified propagation speed of the ultrasonic waves at the component which can be detected with sufficient precision using the method in accordance with the invention and using an apparatus in accordance with the invention.

Figure 3:
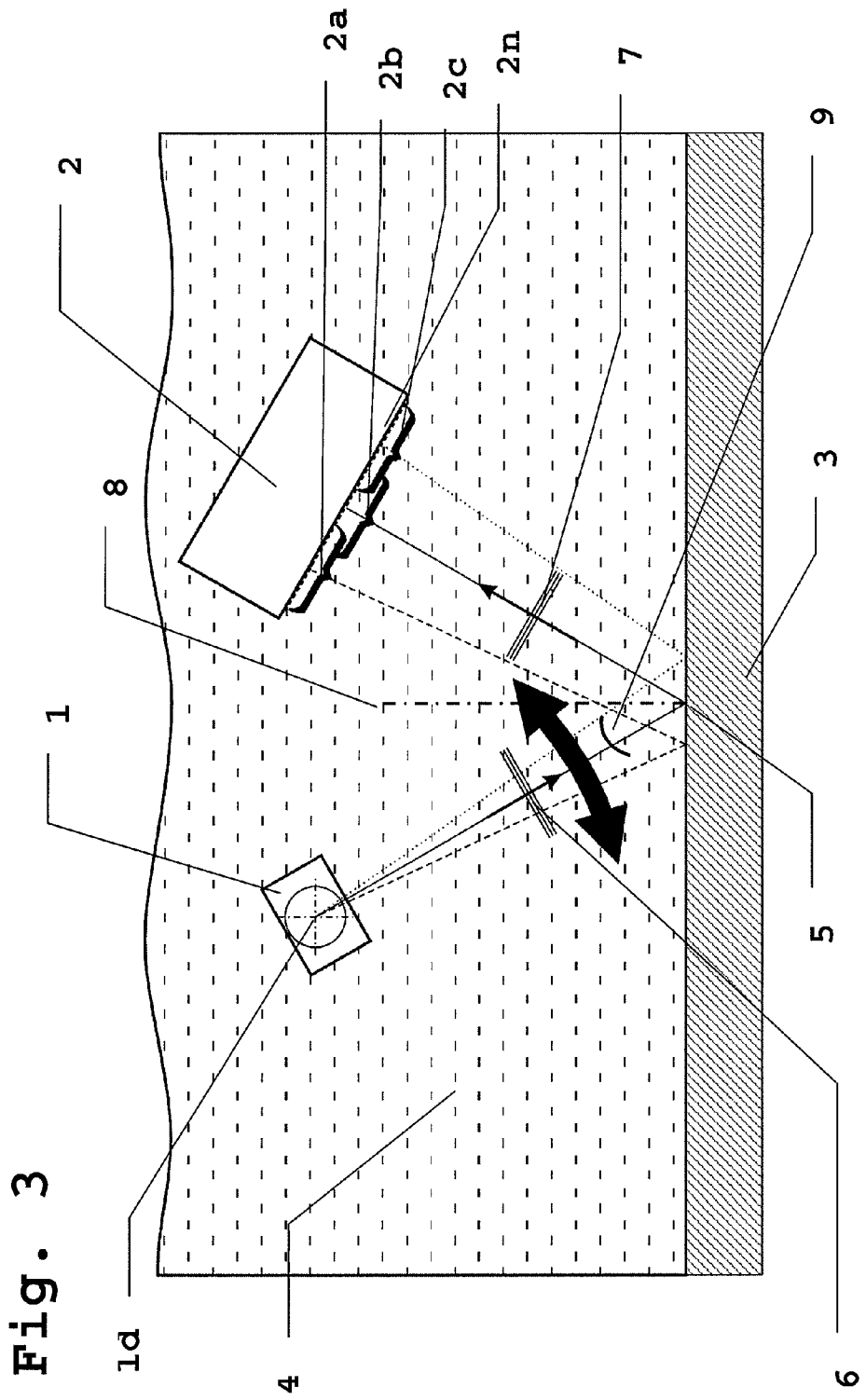
Figure 4:
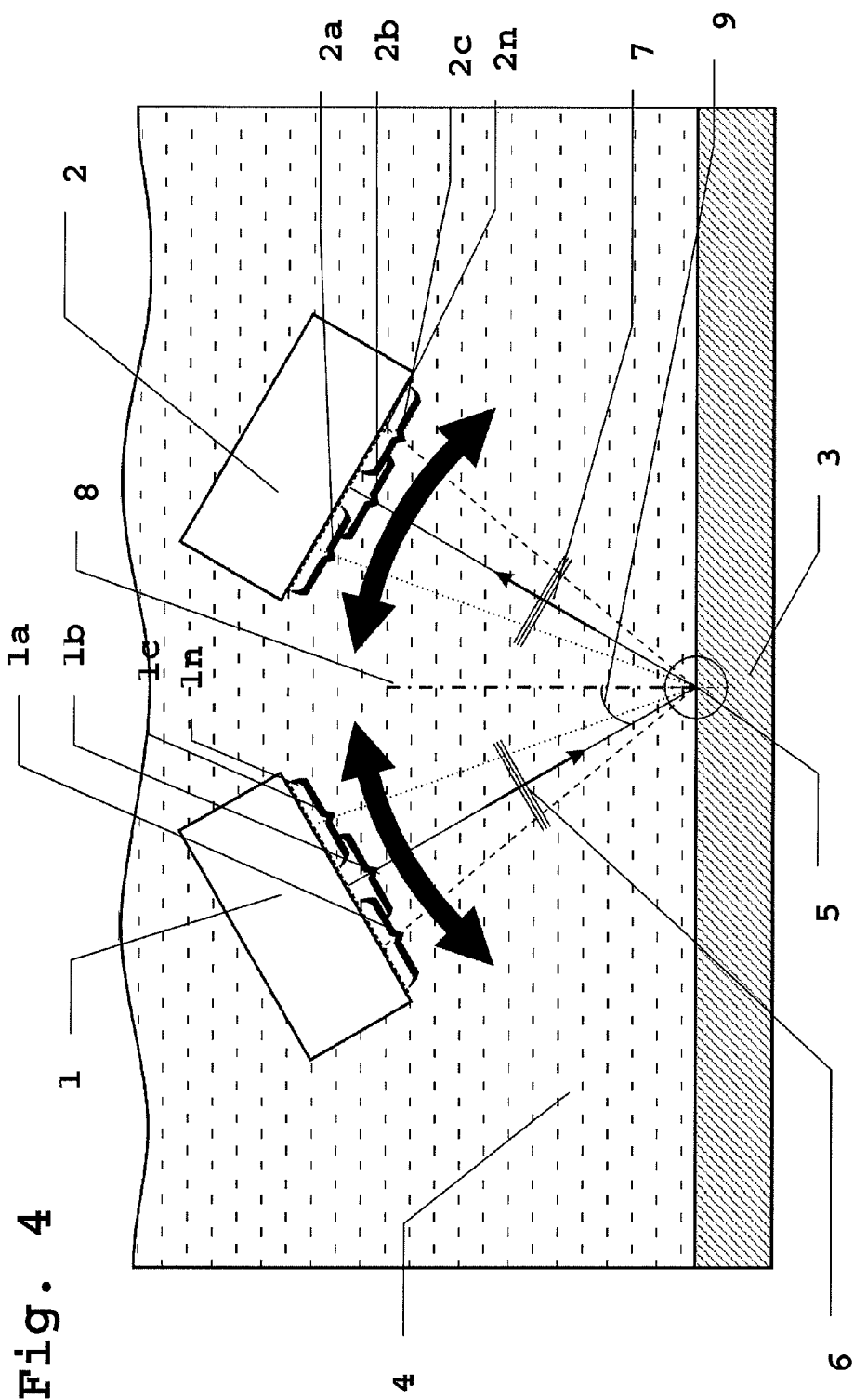

There are shown:

FIG. 1 the design of an ultrasonic goniometer in accordance with the prior art;

FIG. 2 an example of the determined frequency dependence of the propagation speed of the ultrasonic waves guided at the surface of a component;

FIG. 3 an example of an apparatus for carrying out the method in accordance with the invention with an antenna array and a sound transducer configured for emitting ultrasonic waves, with the antenna array not being moved mechanically;

FIG. 4 an example of an apparatus for carrying out the method in accordance with the invention with two antenna arrays, with the antenna arrays not being moved mechanically;

FIG. 5.1 a schematic representation of the emission of an ultrasonic wavefront at an angle using an antenna array; and FIG. 5.2 a schematic representation of the path difference of the ultrasonic waves after an excitation offset in time of individual antenna array elements.

FIG. 1 shows an arrangement of a classical goniometer with two sound transducers 1 and 2. They are arranged at a spacing from the component 3 and its surface in a liquid 4. The sound transducer 1 configured for emitting ultrasonic waves emits ultrasonic waves 6 which are reflected by the surface of the component 3 at the point of incidence 5. The ultrasonic waves 7 reflected by the surface of the component 3 are thereupon detected by a sound transducer 2 configured for detecting ultrasonic waves. In the arrangement in FIG. 1, the two sound transducers 1 and 2 are adjustable symmetrically to the surface normals 8, whereby the angle of irradiation 9 of the ultrasonic waves 6 onto the surface of the component 3 can be modified. The surface of the component 3 can be tested by a frequency-dependent determination of the angle of irradiation 9 having the lowest ultrasonic wave intensity which is incident on the sound transducer 2. In this respect, the position and the orientation of the sound transducers 1 and 2 are respectively varied to measure a new angle of irradiation 9.

FIG. 2 shows an example measurement of three propagation speeds of the ultrasonic waves guided at the surface of the component determined with frequency dependency in meters per second. The measured values of the measured value distribution 11 were determined at a component which was not exposed to any shot peening processing. The measured value distribution 12 was determined at a component exposed to a shot peening intensity of 4 Almen and the measured value distribution 13 was determined at a component which was processed with a shot peening intensity of 8 Almen. A possible use of the method in accordance with the invention for the contactless and nondestructive characterization of the surfaces of components can be recognized from these measured values.

FIG. 3 shows an apparatus in accordance with the invention and an arrangement for carrying out a method in accordance with the invention. Similar to the apparatus shown in FIG. 1, the sound transducer 1 configured for emitting ultrasound waves and the sound transducer 2 configured for detection are arranged above a component 3 in a liquid 4. There is a difference in that the sound transducer 2 is configured as an antenna array having the antenna array elements $2n$. The sound transducer 1 is configured for emitting ultrasonic waves and its angle of inclination for emitting ultrasonic waves can be adjusted by pivoting about a center of rotation $1a$. The angle of irradiation 9 of the ultrasonic waves 6 onto the surface of the component 3 can thereby be varied. The emitted ultrasonic waves 6 are incident on different points of incidence 5 at the surface of the component 3 in dependence on the angle of irradiation 9 and are reflected thereat. The reflected ultrasonic waves 7 are detected by the antenna array 2 configured for detecting ultrasonic waves. In dependence on the angle of incidence 9, the reflected ultrasonic waves 7 are incident on different groups $2a$ to $2c$ of antenna array elements $2n$ of the antenna array 2. In this manner, the propagation speed of the ultrasonic waves guided at the surface of the component 3 can be determined with frequency dependence by a determination of the angle of irradiation 9 with the minimal ultrasonic wave intensity detected at the antenna array 2 and at its antenna array elements $2n$ for every ultrasonic wave frequency of the reflected ultrasonic waves 7.

FIG. 4 shows a further embodiment of an apparatus in accordance with the invention in an arrangement for carrying out a method in accordance with the invention. Both the sound transducer 1 and the sound transducer 2 are in this respect characterized in that they are configured as antenna arrays having the antenna array elements $1n$ and $2n$. The angle of irradiation 9 for the ultrasonic waves 6 onto the surface of the component 3 can be varied by a suitable control of the antenna array elements $1n$ of the antenna array 1 configured for emitting ultrasonic waves in, for example, the antenna array element groups $1a$ to $1c$. The angle β at which the resulting ultrasonic waves 6 are emitted by the antenna array 1 can be varied by a time delay of the excitation of the individual antenna array elements $1n$ in accordance with equation (2).

In the present embodiment, the resulting angle of irradiation 9 is equal to 30 degrees with a simultaneous excitation of all antenna array elements $1n$. The 32 individual antenna array elements $1n$ are arranged at an interval of 0.5 mm. First ultrasonic waves 6 are emitted at an angle of irradiation 9 of 28 degrees in that a time delay Δt of −12 ns between two respective adjacent antenna array elements $1n$ is selected between the maxima of the excitation of the adjacent antenna array elements. A negative time delay in this respect means that the antenna array element 32 is excited before the antenna array element 31 and so on, in each case at a time interval of 12 ns. An angle of irradiation 9 of 32 degrees is set in that the antenna array elements in are excited individually and with at time delay, starting from the antenna array element 1.1, and after 12 ns, followed by the antenna array element 1.2 and after a further 12 ns by the antenna array element 1.3, and so on.

After reflection at the surface of the component 3, the reflected ultrasonic waves 7 are incident on the antenna array 2 configured for detecting ultrasonic waves and having the antenna array elements $2n$. In this respect, the reflected ultrasonic waves 7 are detected by the subsets $2a$ to $2c$ of the antenna array elements $2n$ corresponding to the sets $1a$ to $1c$. If the intensity of the reflected ultrasonic waves is detected for a spectrum of ultrasonic frequencies, the frequency-dependent propagation speed of ultrasonic waves guided at the surface of the component 3 can be determined using the method in accordance with the invention.

FIG. 5.1 illustrates the concept of the form of resulting ultrasonic waves 6 by superimposition of individual ultrasonic waves 6nn which are emitted by the antenna array elements 1n. The angle β is set in this respect by a time-delayed excitation of the antenna array elements 1n to nn. In this respect, similar to the previous embodiment, the antenna array element 1n is first excited to emit the individual ultrasonic waves 6n and finally the antenna array element 1nn emits the ultrasonic waves 6nn. The resulting ultrasonic waves 6 result at an angle β to the plane of the antenna array 1 by a superimposition of the individual ultrasonic waves 6n to 6nn. The angle β is equal to the angle of the ultrasonic wave irradiation direction and the plane normal of the antenna array 1. The angle of irradiation of the ultrasonic waves 6 can in this respect be varied in dependence on the orientation of the antenna array 1 toward the surface of a component.

As an extension to FIG. 5.1, FIG. 5.2 shows four antenna array elements 1.1, 1.2, 1.3 and 1.4 which are arranged at a spacing d at the antenna array 1 and whose individual ultrasonic waves emitted with a time offset have a path difference Δs which the individual ultrasonic waves have covered during the time difference of the excitation of the individual elements 1.1 to 1.4. Resulting ultrasonic waves 6 whose wavefronts propagate at an angle β with respect to the plane of the antenna array 1 arise due to the superimposition of the individual ultrasonic waves. The time delay of the excitation of the individual antenna array elements has to be adapted to the respective antenna array 1 used due to the dependence of the path difference Δs on the spacing of the individual elements d.

The invention claimed is:

1. A method of nondestructive and contactless testing of components (3), wherein ultrasonic waves (6) are irradiated onto a surface of a component (3) at a predefinable, non-perpendicular angle of incidence (9) using an ultrasonic transmission sound transducer (1) spaced apart from the surface of the component (3) and ultrasonic waves (7) reflected from the surface of the component (3) are detected,
characterized in that
an ultrasonic intensity of the ultrasonic waves (7) reflected at the surface of the component (3) detected by antenna array elements (2n) of an ultrasonic antenna array (2) configured for detecting ultrasonic waves (7) is detected, and
a phase shift of the ultrasonic waves irradiated and guided at the surface of the component is determined therefrom with respect to the ultrasonic waves (7) directly reflected at the surface of the component (3).

2. A method in accordance with claim 1,
characterized in that
the ultrasonic intensity is detected with time resolution and/or with frequency resolution and a frequency dependence of a propagation speed of the ultrasonic waves irradiated and guided at the surface of the component (3) is determined therefrom.

3. A method in accordance with claim 1,
characterized in that
the frequency dependence of the propagation speed of the ultrasonic waves irradiated and guided at the surface of the component (3) is determined by the frequency dependence of an ultrasonic wave angle of irradiation (9) which has a minimum of the detected ultrasonic intensity at the antenna array elements (2n) of the ultrasonic antenna array (2) configured for detecting the ultrasonic waves (7) for a respective irradiated ultrasonic wave frequency.

4. A method in accordance with claim 3,
characterized in that
the angle of irradiation (9) at the surface of the component (3) is varied by a temporal and spatial control and/or regulation of an excitation of antenna array elements (1n) of an ultrasonic antenna array (1) configured for emitting ultrasonic waves (6) without a movement of the ultrasonic antenna array (1) that is configured for emitting ultrasonic waves.

5. A method in accordance with claim 1,
characterized in that
the ultrasonic waves (6) irradiated onto the surface of the component (3) are focused in a direction of the surface of the component (3) by a temporal and spatial control and/or regulation of the excitation of an antenna array elements (1n) of an ultrasonic antenna array (1) configured for emitting ultrasound.

6. A method in accordance with claim 1,
characterized in that
a defined spatial and/or temporal intensity distribution of the ultrasonic waves (6) irradiated onto the component (3) is achieved by a temporal and spatial control and/or regulation of an excitation of antenna array elements (1n) of an ultrasonic antenna array (1) configured for emitting ultrasound.

7. A method in accordance with claim 1,
characterized in that
each antenna array element (1n) of an ultrasonic antenna array (1) configured for emitting ultrasound is individually excited for emitting ultrasonic waves (6);
the intensity of the ultrasonic waves (7) reflected from the surface of the component (3) is detected by all antenna array elements (2n) of the ultrasonic antenna array (2) configured for detecting ultrasound; and
the detected ultrasonic intensities are time-resolved and/or frequency-resolved and are superimposed.

8. A method in accordance with claim 1,
characterized in that
the ultrasound wave radiations and the ultrasound wave reflections are carried out by an ultrasonic antenna array (1 or 2) by alternating switching of the ultrasonic antenna array (1 or 2).

9. A method in accordance with claim 1,
characterized in that
the ultrasonic waves (6) radiated by an ultrasonic antenna array (1) which are reflected at the surface of the component (3)
are reflected by a reflector element and the ultrasonic waves (7) reflected in turn at the surface of the component (3) are detected by the or a ultrasonic antenna array (1 or 2) configured for detecting ultrasonic waves.

10. A method in accordance with claim 9,
carried out using exactly one ultrasonic antenna array.

11. A method in accordance with claim 1,
characterized in that
the radiated ultrasonic waves are directed to the component (3) arranged in a liquid bath (4).

12. An apparatus for carrying out the method in accordance with claim 1, comprising at least one ultrasonic transmission sound transducer or antenna array (1) configured for radiating ultrasonic waves and at least one antenna array (2) configured for detecting reflected ultrasonic waves (7),
characterized in that the ultrasonic transmission sound transducer (1) is configured for varying an angle of incidence (9) of the ultrasound waves (6) onto the surface of the component (3);

and/or in that the apparatus has an ultrasonic antenna array (1) configured for emitting ultrasonic waves (6);

and in that an ultrasonic antenna array (2) is configured for detecting the reflected ultrasonic waves (7).

13. An apparatus in accordance with claim 12, characterized in that the apparatus has the ultrasonic sound transducer (1) configured for emitting ultrasonic waves (6) which is configured for adjusting the angle of inclination of its ultrasonic wave emission on the surface of the component (3);

and includes an ultrasonic antenna array (2) configured for detecting reflected ultrasonic waves (7).

14. An apparatus in accordance with claim 12, characterized in that the apparatus has an ultrasonic antenna array (1 or 2)

which is configured for switching between ultrasonic wave radiation and ultrasonic wave detection, and has an ultrasonic reflector element.

15. An apparatus in accordance with claim 12, characterized in that the ultrasonic antenna array(s) (1, 2) is/are configured as line antenna arrays and/or as matrix antenna arrays and/or as ring antenna arrays.

16. Use of an apparatus in accordance with claim 12, for characterizing surface coatings and/or surface processing states of surface-strengthened components.

* * * * *